(12) United States Patent
Kittappa et al.

(10) Patent No.: US 10,160,951 B2
(45) Date of Patent: Dec. 25, 2018

(54) STEM CELLS FROM THE MAMMALIAN NEURAL PLATE

(71) Applicant: Raja Kittappa, Mountville, PA (US)

(72) Inventors: Raja Kittappa, Mountville, PA (US); Austin Smith, Great Shelford (GB)

( * ) Notice: Subject to any disclaimer, the term of this patent is extended or adjusted under 35 U.S.C. 154(b) by 0 days.

(21) Appl. No.: 14/395,257

(22) PCT Filed: Apr. 16, 2013

(86) PCT No.: PCT/GB2013/050967
§ 371 (c)(1),
(2) Date: Oct. 17, 2014

(87) PCT Pub. No.: WO2013/156768
PCT Pub. Date: Oct. 24, 2013

(65) Prior Publication Data
US 2015/0132850 A1    May 14, 2015

(30) Foreign Application Priority Data
Apr. 17, 2012  (GB) .................................. 1206773.2

(51) Int. Cl.
*C12N 5/00* (2006.01)
*C12N 5/0797* (2010.01)

(52) U.S. Cl.
CPC ...... *C12N 5/0623* (2013.01); *C12N 2501/115* (2013.01); *C12N 2501/119* (2013.01); *C12N 2501/16* (2013.01); *C12N 2506/02* (2013.01); *C12N 2506/025* (2013.01); *C12N 2506/45* (2013.01)

(58) Field of Classification Search
CPC .... A61K 35/30; A61K 35/54; A61K 38/1825; A61K 38/18; A61K 47/6891; G01N 33/68; G01N 33/5073; G01N 33/56966; G01N 2333/705; G01N 2500/10; G01N 33/5005; G01N 33/5058
See application file for complete search history.

(56) References Cited

U.S. PATENT DOCUMENTS 6,277,820 B1    8/2001 Rosenthal et al.
2002/0151054 A1    10/2002 Rathjen et al.

FOREIGN PATENT DOCUMENTS

WO    WO-01/51611 A1    7/2001

OTHER PUBLICATIONS

Ye et al., Cell, 93:755-766, May 29, 1998.*
Kunisada et al., Birth Defects Res C Embryo Today, 102(3):251-262, Sep. 2014.*
Iwafuchi-Doi et al., Dev Biol, 352:354-366, 2011.*
Zhang et al., BioMed Research International, vol. 2015, Article ID 727542, 14 pages, Epub Sep. 1, 2015.*
Dominguez et al., Cerebral Cortex Nov. 2013;23:2632-2643, Epub Aug. 14, 2012.*
Temple, Nature, 414:112-117, 2001.*
Sansom and Livesey, Cold Spring Harb Perspect Biol 2009;1:a002519.*
Qian et al., Neuron, vol. 28, 69-80, Oct. 2000.*
Kosaka et al., "FGF-4 regulates neural progenitor cell proliferation and neuronal differentiation," FASEB J. 20(9):e623-9, 1484-5 (2006).
Kosaka et al., "Pleiotropic function of FGF-4: its role in development and stem cells," Dev Dyn. 238(2):265-76 (2009).
Kunath et al., "FGF stimulation of the Erk1/2 signaling cascade triggers transition of pluripotent embryonic stem cells from self-renewal to lineage commitment," Development. 134(16):2895-902 (supplemental figures 1 and 2 are provided) (2007).
Sterneckert et al., "Neural induction intermediates exhibit distinct roles of Fgf signaling," Stem Cells. 28(10):1772-81 (2010).
Villegas et al., "FGF signaling as a mediator of lineage transitions-evidence from embryonic stem cell differentiation," J Cell Biochem. 110(1):10-20 (2010).
International Search Report for International Application No. PCT/GB2013/050967, dated Jul. 23, 2013 (4 pages).

* cited by examiner

*Primary Examiner* — Kimberly Ballard
*Assistant Examiner* — Stacey N MacFarlane
(74) *Attorney, Agent, or Firm* — Quarles & Brady LLP

(57) ABSTRACT

The present invention relates to methods for deriving novel stem cells from the mammalian early neural plate.

18 Claims, 18 Drawing Sheets

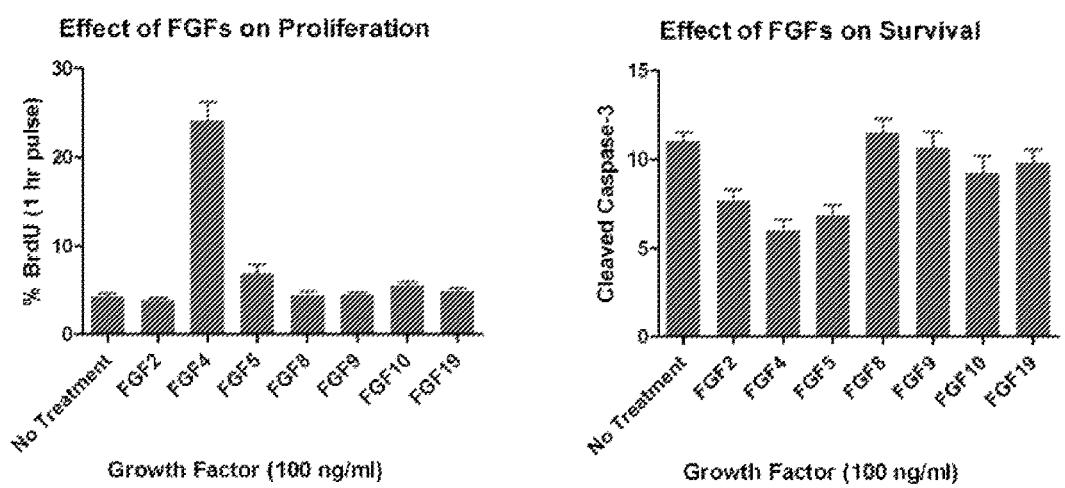
Figure 1: The effects of FGFs on Proliferation and Survival of E7.5 CNS Progenitors Figure 2: *In vitro* Culture of E8.5 Neural Stem Cells
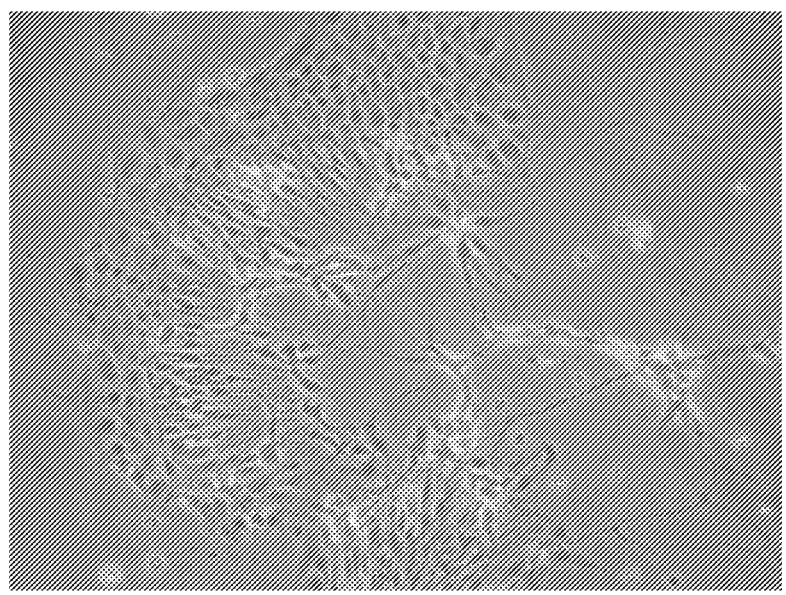

Figure 3: Production of NPSCs from pluripotent cells
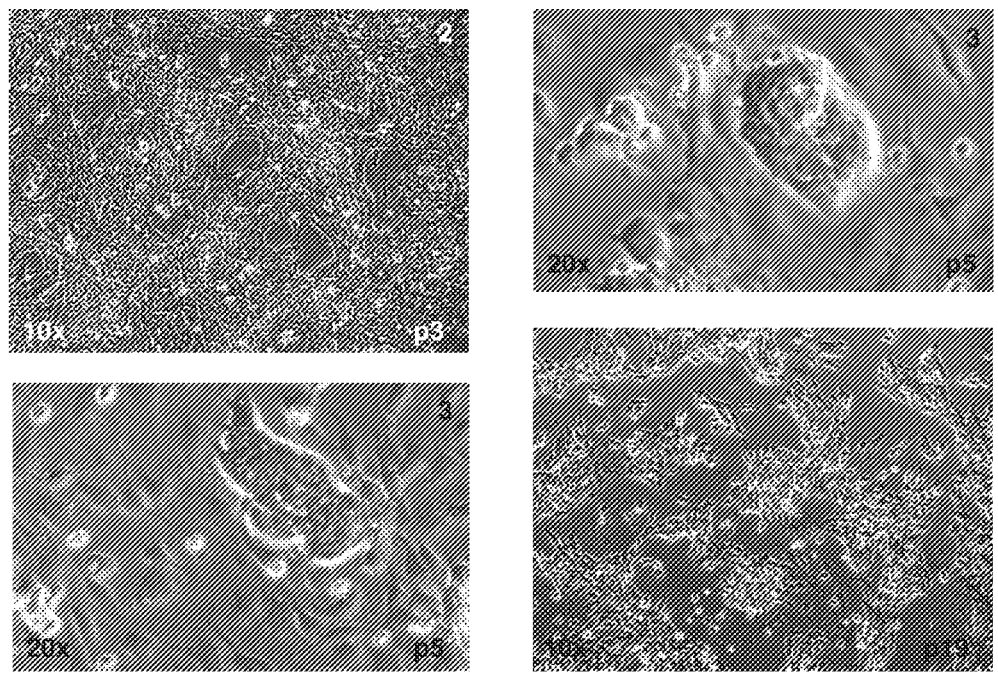

Figure 4: Methods for producing NPSCs from epiblast cells
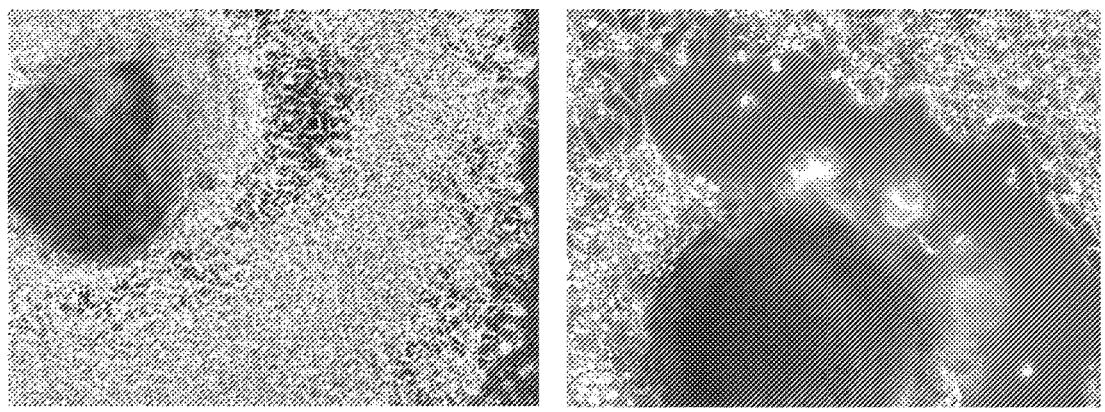

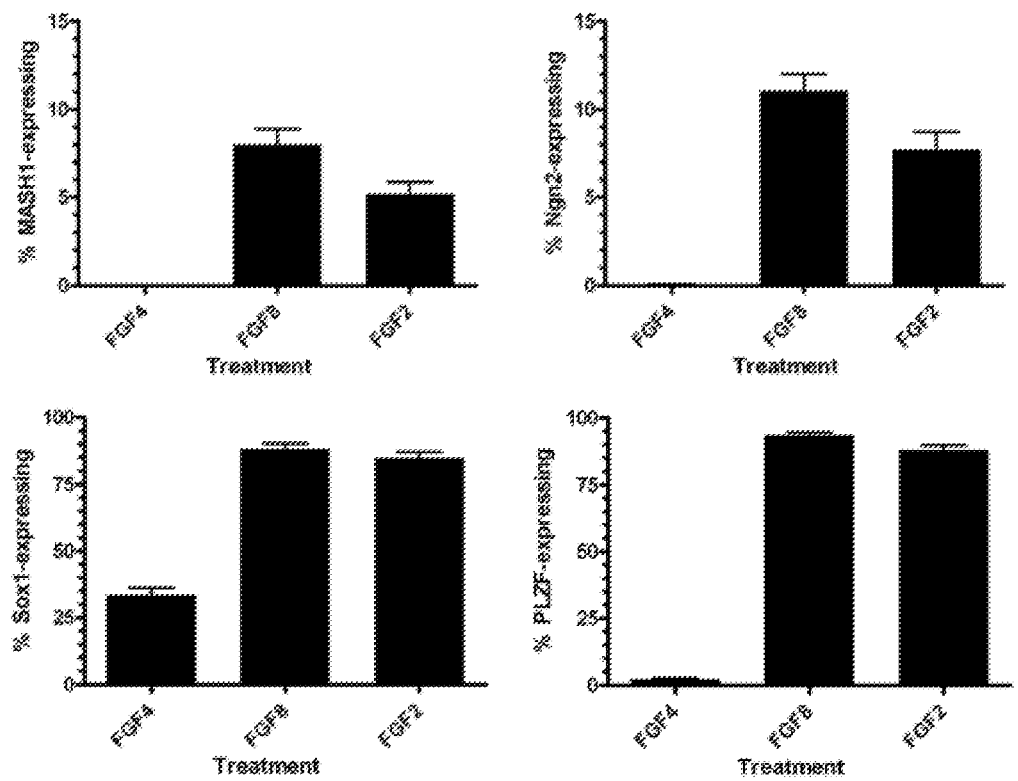

Figure 6: Derivation of Neural Progenitors from Human ES Cells.
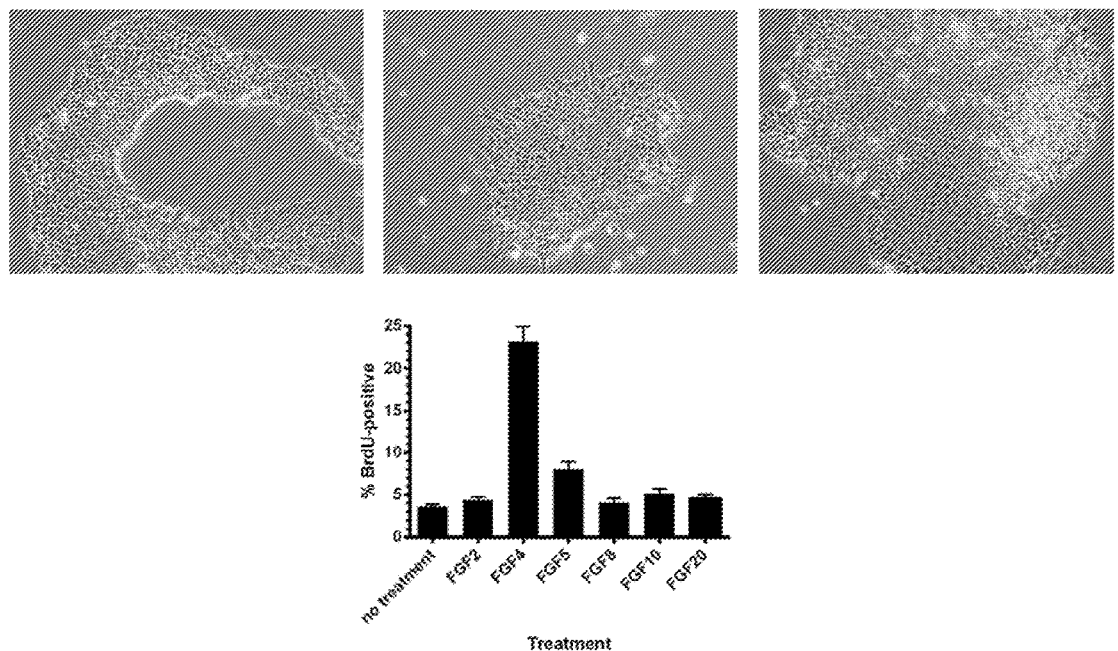

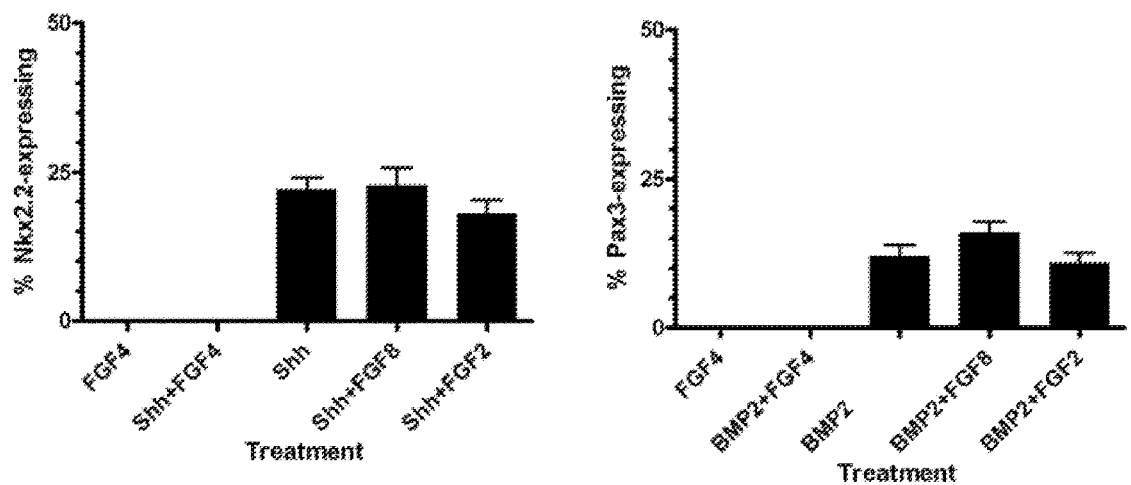
Figure 7: FGF4 Suppresses the Morphogenic Response of Shh and BMP2

Figure 8: Differentiation of NPSCs to Neurons in the absence of FGF4
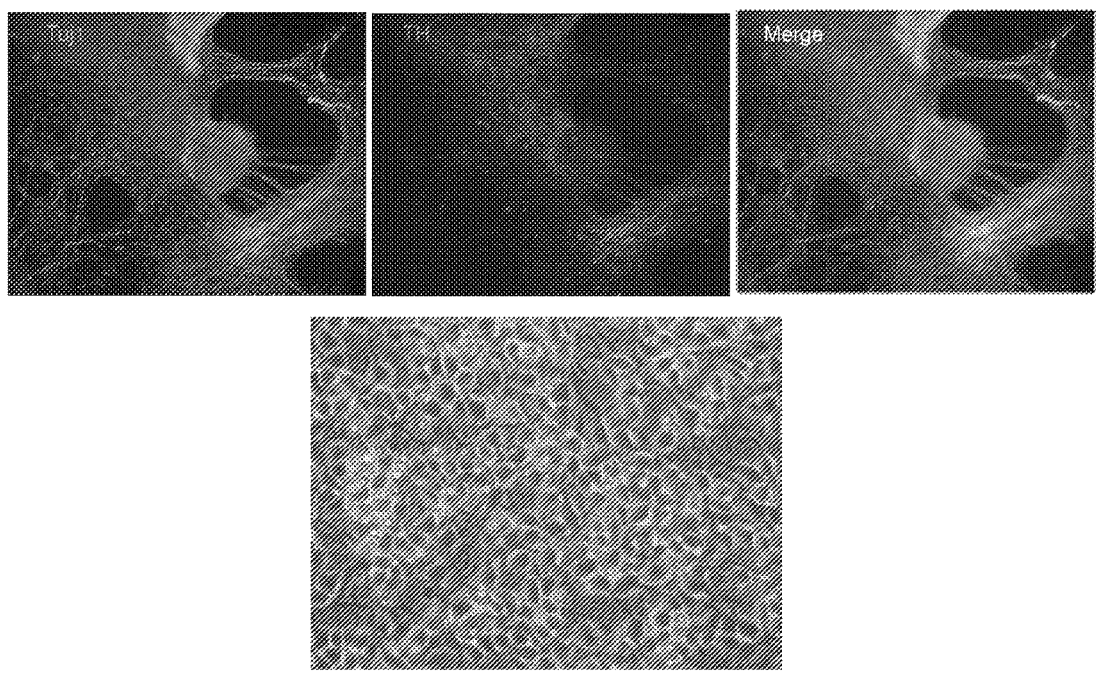

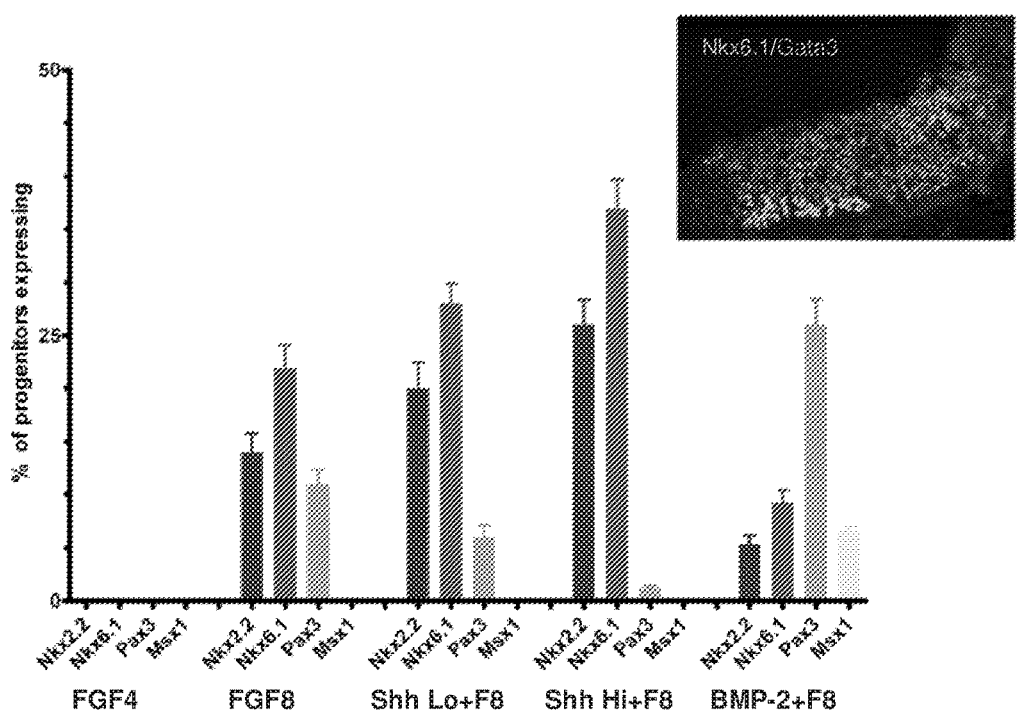
Figure 9: Induction of Dorsoventral Identities by Morphogens in the Absence of FGF4

Figure 10: Treatment with Shh leads to an Increase in Monoaminergic Neurons
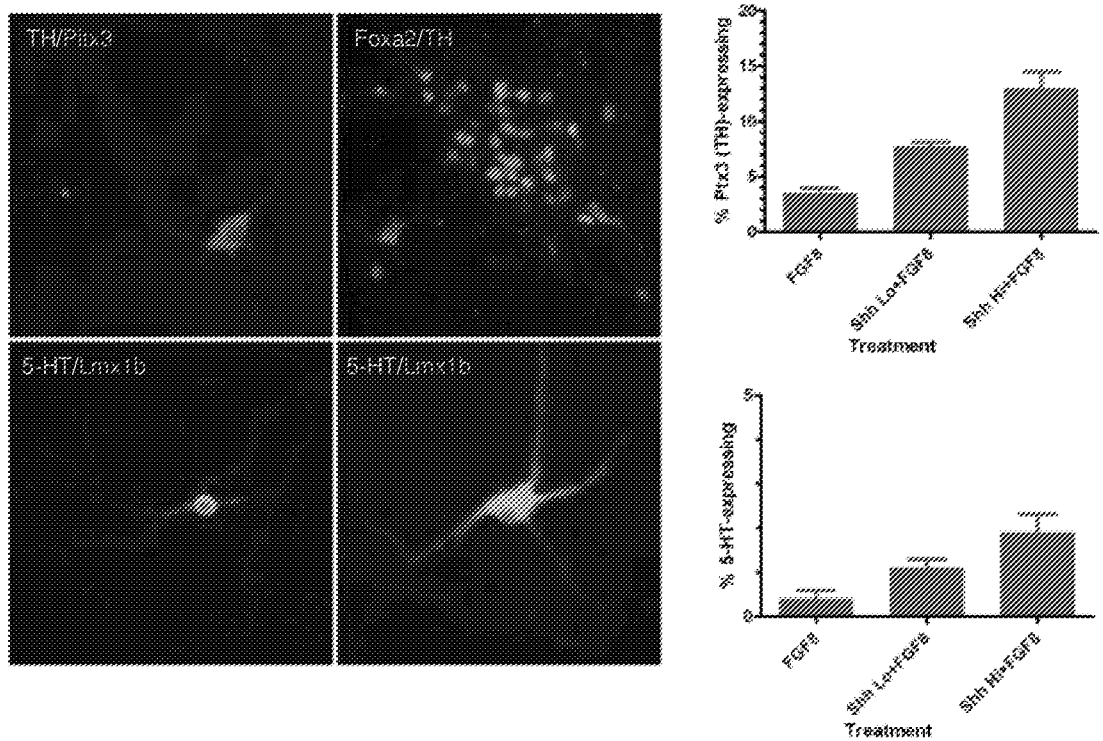

Figure 11: Retinoic Acid-Treated Progenitors Differentiate to Putative Motor Neurons
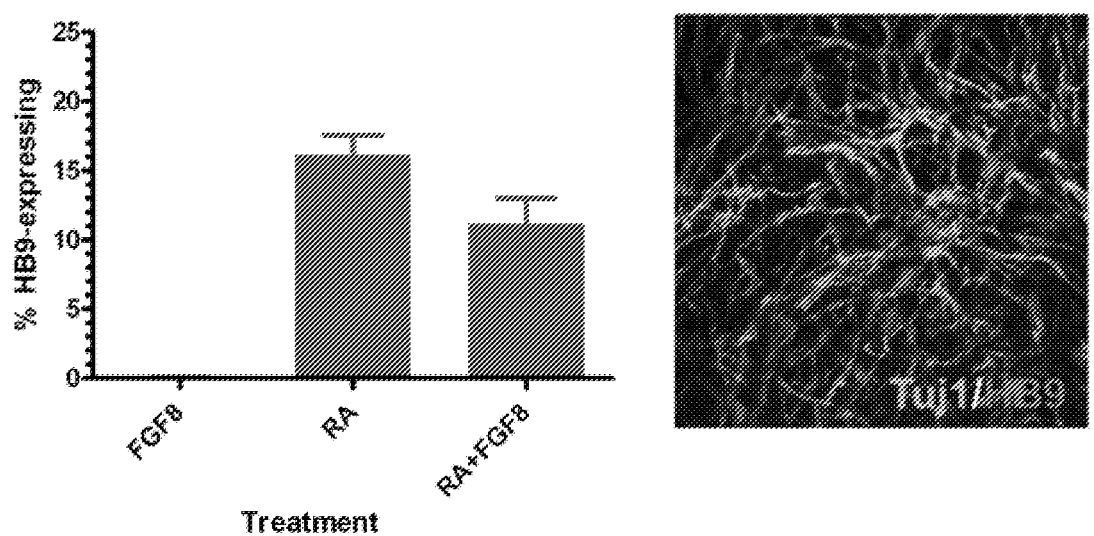

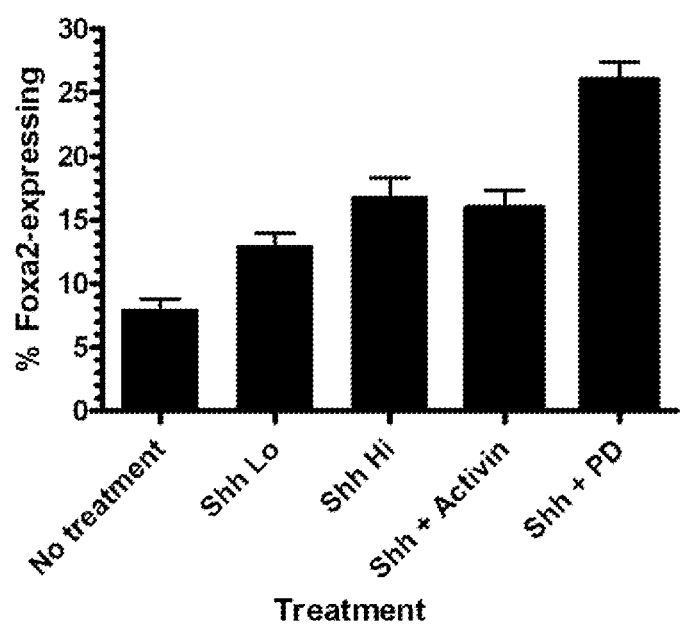
Figure 12: Floor Plate induction of neural plate cells gives rise to dopamine neurons

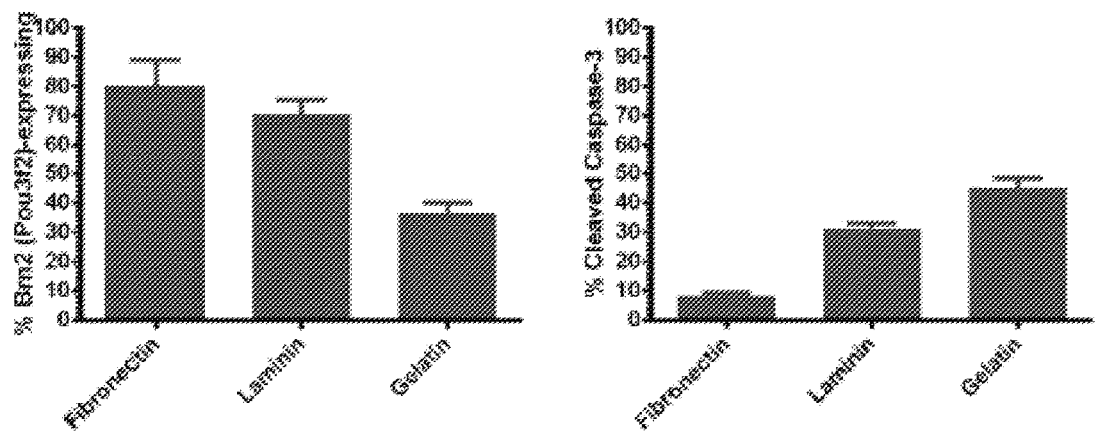
Figure 13: Derivation of Neural Plate Stem Cells on a variety of extracellular matrices in monolayer culture Figure 14: Clonal growth of neural plate stem cells
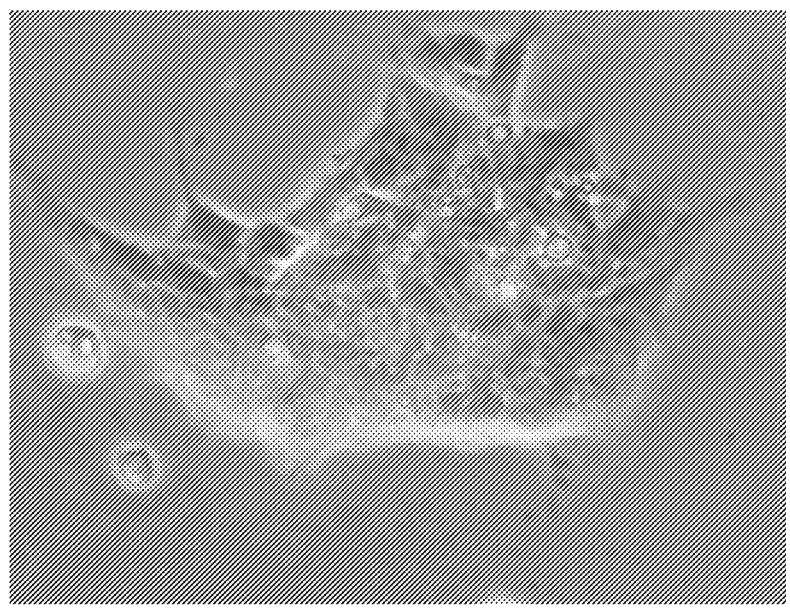

Figure 15: Expression of Sox1 and Brn2 in the Neural Plate
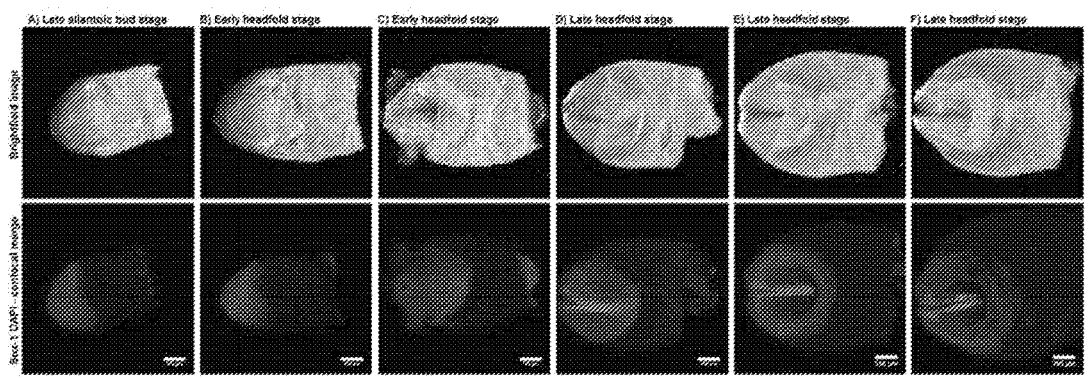

Figure 15A: Expression of Sox1 and Brn2 in the Neural Plate
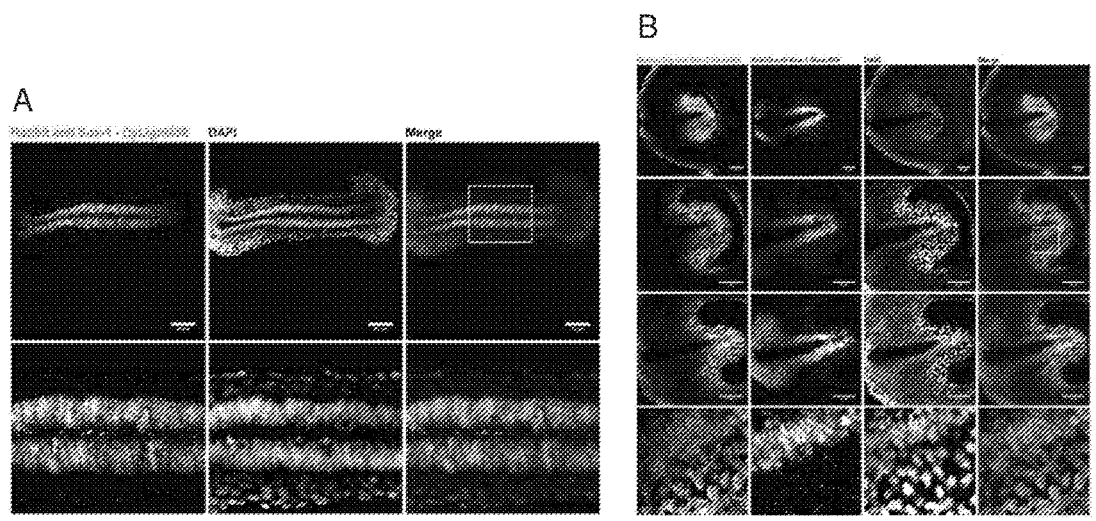

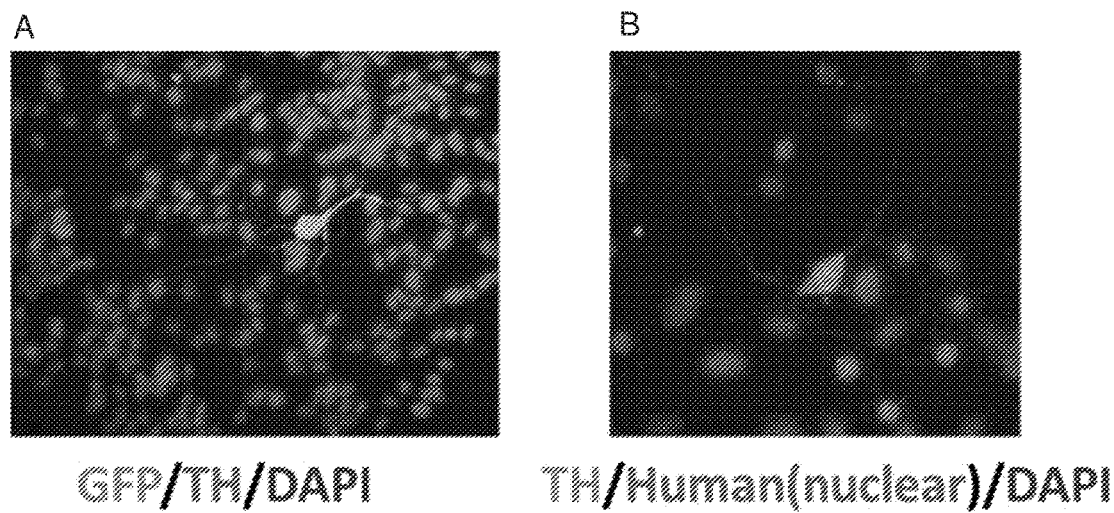
Figure 16: Transplantation to Chick Embryo

Figure 17: Transplantation into Neonatal Rat Hindbrain
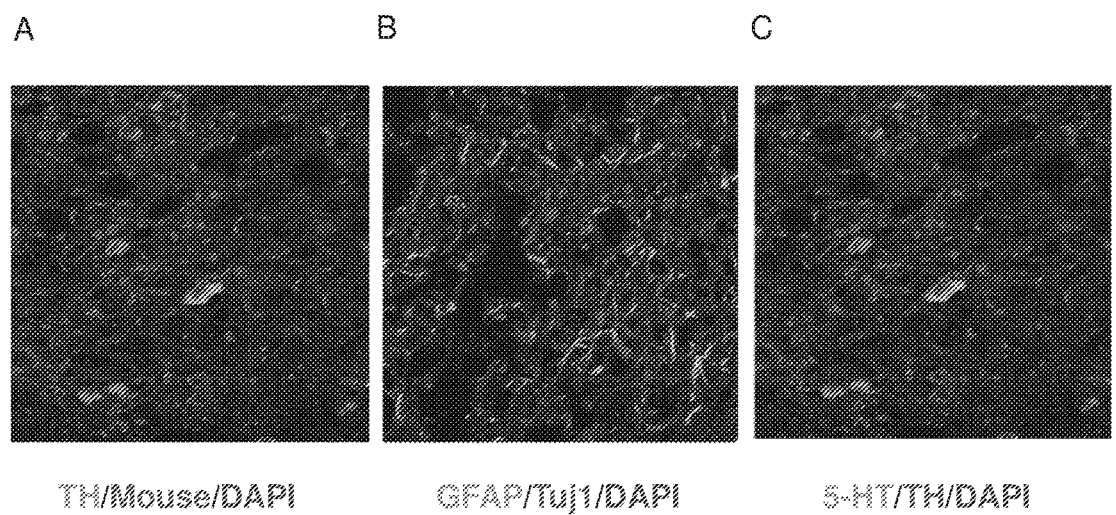

STEM CELLS FROM THE MAMMALIAN NEURAL PLATE

DECLARATION

The work leading to this invention has received funding from the European Research Council under the European Union's Seventh Framework Programme (FP7/2007-2013)/ERC grant agreement no 222943.

TECHNICAL FIELD

The present invention relates to methods for deriving stem cells from the mammalian early neural plate (Neural Plate Stem Cells—NPSCs), methods for deriving NPSCs from pluripotent cells, to NPSCs obtained by these methods and to NPSCs per se.

BACKGROUND

Almost all animals from sea urchins to fruit flies, to fish and frogs, to mice and men undergo a process called gastrulation in their early embryonic life. During gastrulation, pluripotent cells involute to the centre of the embryo. The cells allocated in this manner are destined to form layers of more specialized embryonic cells, the mesoderm and the endoderm. The mesoderm will form blood and the musculoskeletal system. The endoderm will form the digestive tract and associated internal organs.

Shortly following gastrulation, the embryo undergoes neurulation. In vertebrates, the hallmark of neurulation is the establishment of the neural plate from pluripotent cells. The neural plate bends ventrally at its midline causing the edges to come together and form a tube. All of the cells of the central and peripheral nervous system are derived from the neural plate and neural tube. The cells of the neural plate are the first cells to become committed to the neural lineage.

The ability to study these early neural cells in more detail would provide valuable information relating to numerous neurodevelopmental and neurodegenerative disorders. At present, over ten million people, worldwide are afflicted by neurodegenerative disorders, including Alzheimer's disease, Parkinson's disease, Amyotrophic Lateral Sclerosis, and Huntington's Disease. Thus, there is considerable interest in the development of stem cell models and therapies to remedy the effects of neurodegenerative disease.

Neural cell types can be generated from pluripotent stem cells; however, the differentiation of embryonic stem cells requires multiple steps and does not often efficiently generate the specific neurons lost in neurodegenerative disease. An attractive alternative would be stem cell lines already restricted to the neural lineage that could be rapidly differentiated to neurons of clinical interest. In addition, cultured neural stem cell lines would provide a means to study human neurodevelopment.

Derivation of Neural Stem Cell Lines

Evidence that neural stem cells could be maintained in vitro was provided by Reynolds Tetzlaff and Weiss 1992; culture of 14 day old striata with the growth factor EGF was reported to lead to the propagation of stem-cell comprising floating cell clusters ("neurospheres"). However, neurospheres consist predominately of committed neural progenitors and differentiated cells, with the maintained stem cells not being directly identifiable or purified. Moreover, the stem cells maintained in neurospheres have an uncertain relationship to CNS precursor cells in vivo.

Later studies showed that cells within the neurospheres were responsive to bFGF (Vescovi et al 1993), with the application of bFGF leading to the proliferation of two progenitor cell types. Further experiments demonstrated that neural precursor cells could be propagated from adult mouse striatum by culture with bFGF (Gritti et al 1996), from the lumbar/sacral segment of the spinal cord with EGF+bFGF (Weiss et al 1996), and in adherent cultures when cultured with the growth factor FGF2 (Johe et al 1996).

Rathjen et al. 2002 (and also in U.S. patent application Ser. No. 10/090,849; publication number US2002/0151054 A1) report the derivation of a neuroectodermal lineage which is described as "multipotential" and having the capacity to differentiate into a number of neuronal cell types, including neuronal cells, glial cells and neural crest cells. However, the cells described in Rathjen are shown to express the neurogenic bHLH factor mash1, and the marker of BMP-2 activity, pax3. Pax3, in particular, is an indicator of dorsoventral patterning, indicating that the cells in Rathjen are partially differentiated.

Conti et al 2005 report the derivation and maintenance of a neural stem cell (NS cell) monoculture through culturing cells in N2 media supplemented with the growth factors FGF2 and EGF. Conti et al report that the addition of both FGF 2 and EGF is critical for the continued propagation of the NS cells which they had derived.

The NS cells' characteristics indicate they are closely related to the radial glia lineage, with uniform and stable expression of neurogenic basic Helix-loop-Helix (bHLH) factors such as olig2 and mash1, and limited ability to differentiate into neuronal cell types.

The Role of FGF2 and FGF4

In addition to the above described role in promoting the proliferation of neural progenitor cells, FGF2 has also been reported to promote the differentiation of embryonic stem cell into neural fates. For example, Forsberg et al 2012 report that the addition of FGF2 and heparin to NDST 1/2 negative murine ES cells restored the ability of the ES cells to differentiate into neural cell types. The ability to restore neuronal differentiation was also seen on addition of FGF4 and heparin.

FGF2 and FGF4 have also been reported to induce proliferation of cells in an in vitro neurosphere assay (Kosaka et al 2006). In this assay, primary germinal zone cells from the ganglionic eminence of an E14 mouse embryo were cultured in the presence of either FGF2 or FGF4. It was found that both FGF2 and FGF4 led to an increase in the number of neurospheres which were formed, along with an increase in cell viability.

In the same paper, Kosaka et al also report that FGF4 induces differentiation of EGF-responsive stem-cell progeny in a manner comparable to that of FGF2, leading them to propose FGF4 as a key inducer of neuronal differentiation. This latter proposition is consistent with the results reported by Chen et al 2010, where both FGF4 and FGF2 are shown to lead to significantly elevated neural induction in '46C' mouse ES cells (GFP-Sox1 knock-in).

As well as its reported function in promoting the differentiation of neural cell types from ES cells, FGF4 has been reported to promote the maintenance of some (non-neural) stem cell types.

Tanaka et al 1998 reported the isolation of permanent trophobalst stem (TS) cell lines by culturing mouse blastocysts or early post-implantation trophoblasts in the presence of FGF4. This result was subsequently confirmed by Abell et al 2009, who further characterized the mechanism by which FGF4 maintains TS cells as employing the MEKK4 kinase as a signalling hub.

FGF4 has also been reported to support the undifferentiated growth of human ES cells (Mayshar et al 2008). Targeted knockdown of FGF4 expression in these cells was observed to lead to increased differentiation of the hES cells.

However, as indicated above, the differentiation of embryonic stem cells requires multiple steps and does not often efficiently generate the specific neurons that are sought. Of the neural stem cell lines currently available, none is of a sufficiently early developmental stage to allow differentiation into every neural cell type. For example, NS cells arederived from embryonic day 12 (E12) onwards, whereas dopaminergic neurons (of interest in Parkinsons disease, for example) are already differentiated by stage E11.5 (nb. Staging relates to mouse embryos). In addition, a neural stem cell line from a very early stage would allow the modelling of early-stage neural defects, such as neural tube defects (NTDs). Finally, the availability of an early neural stem cell line would give researchers much more control over the process of neural development and the ability to study and direct differentiation.

Thus, there is a need for the development of a neural stem cell line from an early stage of neural development which is capable of differentiation into a broad range of neuronal subtypes and glia.

DISCLOSURE OF THE INVENTION

The present invention provides methods for deriving a neural stem cell lineage from a very early stage in neural development. An object of the invention is to provide a neural stem cell line which can be stably and indefinitely maintained at an early developmental stage and which can be subsequently differentiated into a broad range of neuronal cell types.

In various aspects of the invention described below the inventors have used primitive cells from a variety of sources (primary embryonic cells dissected from the neural plate, embryonic stem (ES) cells, induced pluripotent (iPS) cells, mouse epiblast stem cells) as a starting point from which to derive novel Neural Plate Stem Cells (NPSCs). The key step in the derivation process from all cell types is culturing in the presence of the growth factor FGF4.

Once derived, the NPSCs can be stably and indefinitely maintained in an undifferentiated state by continued culture in the presence of FGF4 and in the absence of FGF2 and EGF.

Whilst cultured in the presence of FGF4, NPSCs are maintained in a 'pre-patterning' state, where they do not express neurogenic factors such as PLZF, Ngn2, MASH1, Pax3, Pax6, En1, En2, or Krox20 and they are not responsive to the dorsoventral patterning signals of Sonic hedgehog (Shh) and BMP-2.

Once FGF4 is removed, Shh and BMP-2 are able to properly induce dorsoventral identities and the NPSCs differentiate into neurons. This change can also be observed by the loss of the NPSCs epithelial morphology and their formation into neural rosettes (which are characteristic of later neural cells from the neural tube) which subsequently differentiate into neurons; this change can also be observed by the onset of induction of markers such as pax3. The NPSCs retain the ability to differentiate into dopamine and serotonin neurons, as well as motorneurons, even after numerous passages.

The role of FGF4 in the proliferation of NPSCs is unexpected. The proliferation and stem cell state of neural precursors from older embryos and the adult have consistently been shown to be supported by two growth factors, FGF2 and EGF. Interestingly, neither FGF2 nor EGF have any effect on the proliferation of neural plate stem cells. Of the growth factors tested, only FGF4 supports the proliferation and stem cell state of NPSCs. A specific effect for FGF4 has not been shown previously for any neural precursor or stem cell.

By using FGF4 to capture the neural plate stem cell state, the inventors have derived neural plate cell lines from several different pluripotent cell types, including mouse epiblast cells, human embryonic stem (hES) cells, and human induced pluripotent stem (hIPS) cells.

The inventors have also characterized the expression of neural markers in NPSCs.

The Sry-box-containing transcription factor, Sox1, was previously described as the earliest marker of the neural lineage in fish and in frogs. Surprisingly, Sox1 is observed to only be expressed in about 30% of the NPSC population. Examination of the NPSC population has not revealed any difference in phenotype or cell behaviour for Sox1+ as compared to Sox1− NPSCs.

In contrast, when FGF4 is removed, within 48 hours the resulting neural rosettes almost uniformly express Sox1. In parallel, known neurogenic bHLH transcription factors, like MASH-1 and Neurogenin-2 (Ngn-2), are also not expressed in neural plate stem cells but are transiently upregulated when FGF4 is withdrawn. Similarly, the zinc-finger marker PLZF and the markers Pax3, Pax6, En1, En2, and Krox20 are not expressed in NPSCs.

The inventors have also examined gene expression in the early mouse neural plate. Surprisingly, Sox1 is not expressed in the early neural plate. When Sox1 is turned on in the intermediate neural plate, its expression is restricted to the ventral midline of the neural plate. At late neural plate stages, Sox1 expression widens but it is still not expressed in all neural plate cells.

In contrast to Sox1, the inventors have found that the homeodomain containing transcription factor, Brn2 (also called Pou3f2) is expressed throughout the neural plate from the earliest stages. In addition, Brn2 is also expressed uniformly throughout NPSCs in vitro. Numerous groups have shown Sox1 expression in stem cells that they have derived from older embryos. The inventors now show that Brn2, not Sox1, is the earliest marker of the neural lineage and that, unlike Sox1, it is expressed throughout the intact neural plate and uniformly in neural plate stem cells.

Some aspects of the present invention will now be discussed in more detail.

Methods of Obtaining NPSCs

The key factor in deriving NPSCs from precursor cells (e.g pluripotent cells or primitive neurectodermal cells) is culturing the precursor cells in the presence of FGF4. This is a new and surprising feature of a neural stem cell line and is characteristic of NPSCs. The proliferation and stem cell state of neural precursors from older embryos and the adult have consistently been shown to be supported by two growth factors, FGF2 and EGF; neither FGF2 nor EGF have any effect on the proliferation of neural plate stem cells.

Accordingly, the invention provides a method of obtaining a neural plate stem cell, comprising:—
(a) providing a pluripotent cell or primitive neurectodermal cell;
(b) culturing the cell population in the presence of FGF4; and (c) thereby obtaining a neural plate stem cell,
wherein FGF4 increases the proliferation of the NPSC and FGF2 does not increase the proliferation of the neural plate stem cell.

The derivation of some known neural precursor populations are reported to require culturing on a specific substrate; for example, in U.S. patent application Ser. No. 10/090,849 Rathjen et al. indicate a requirement for cellular fibronectin. In contrast, the present inventors have found that derivation of NPSCs is possible using a variety of extracellular matrices during culture, for example fibronection, laminin or gelatin (see FIG. 13). Accordingly, in some embodiments, the neural plate stem cell are cultured in the presence of fibronectin, laminin or gelatin; for example, fibronectin, laminin or gelatin may be present as the sole component of an extracellular matrix upon which the NPSCs are cultured. In some embodiments, the neural plate stem cell is cultured in the absence of fibronectin, laminin or gelatin. In some embodiments, the neural plate stem cell is cultured in the absence of fibronectin.

In some embodiments, the rate of proliferation of the NPSC in the presence of FGF4 is more than twice the rate of proliferation observed in the absence of exogenous growth factors (e.g. the rate of proliferation observed for NPSC cultured only in N2 medium). For example, the rate of proliferation of the NPSC in the presence of FGF4 may be more than three-fold the rate of proliferation observed in the absence of exogenous growth factors, such as more than four-fold, more than five-fold, or more than 6-fold. Proliferation of the NPSC may be measured by, for example, measuring the proportion of cells which incorporate Bromodeoxyuridine (BrdU) in a defined time window (see, for example, FIG. 1).

The invention also provides a method of obtaining a neural plate stem cell, comprising:—
(a) providing a pluripotent cell or primitive neurectodermal cell;
(b) culturing the cell population in the presence of FGF4; and
(c) thereby obtaining a neural plate stem cell,
wherein FGF4 maintains the NPSC in a pre-patterning state and FGF2 does not maintains the NPSC in a pre-patterning state.

In this respect, a "pre-patterning state" is a state where the NPSC expresses the marker Brn-2 and does not express the neurogenic bHLH factors Ngn2 and MASH1. In the pre-patterning state the NPSC does not express the markers Pax3; the markers Pax6, En1, En2, and/or Krox20 are also not expressed. In the "pre patterning state, the NPSC is not responsive to the dorsoventral patterning signals of Sonic hedgehog (Shh) and BMP-2.

The obtained NPSCs can be passaged with Accutase or collagenase. Passaging with collagenase maintains the epithelial morphology of the cells while passaging with accutase does not. However, Accutase passaged NPSCs remain functionally equivalent to NPSCs passaged with Accutase. In some embodiments the NPSCs can be passaged for at least 40 passages and still maintain the characteristic NPSC properties described herein.

Typically, the pluripotent cell is cultured in serum-free media, such as N2 media (Bottenstein and Sato, 1979), to which the required growth factors (e.g. FGF4) are added.

In some embodiments, the pluripotent cell or primitive neurectodermal cell may be cultured in the presence of FGF2 and/or Activin prior to the addition of FGF4.

In some embodiments the pluripotent cell is cultured in the presence of FGF4, FGF2 and activin until cells with a neural morphology are observed. Upon observing cells with a neural morphology, FGF2 and/or activin may be removed from the culture medium (i.e. the cells are then cultured in the absence of FGF2 and/or activin). In practice, "removal" of FGF2 and/or activin is achieved by replacing the medium containing FGF2 and/or activin with medium containing, in this case, only FGF4.

In other embodiments the pluripotent cell or primitive neurectodermal cell is cultured in the absence of FGF2 and/or Activin. In some embodiments, FGF4 is the only FGF present in the culture medium. In some embodiments FGF4 is the only growth factor present in the culture medium. In other embodiments the medium consists of FGF4 as the active ingredient. In yet other embodiments the medium consists essentially of FGF4 as the active ingredient. In this context "active ingredient" is used to mean that ingredient intended to select or maintain the preferred (e.g. NPSC) cell population.

The present invention provides an isolated neural plate stem cell, or population of such cells, obtained by the methods described herein.

The present invention further provides for the use of a medium comprising FGF4 in a method as described herein, for obtaining a neural plate stem cell.

Also provided by the present invention is a method of deriving a neural plate stem cell population substantially as hereinbefore described with reference to any of the Examples herein.

Preferred Precursor Cells for the Derivation of NPSCs

The pluripotent cell or primitive neurectodermal cell from which the NPSCs is derived is preferably mammalian, in particular mouse, rat, primate, non-human primate, ovine, bovine, porcine or human. The examples herein used mouse or human cells. Preferably, the cell is a human cell. However application of the present invention to avian cells is also encompassed.

NPSCs may be derived from a broad range of starting pluripotent cells or primitive neurectodermal cell (primary embryonic cells dissected from the neural plate, embryonic stem (ES) cells, induced pluripotent (iPS) cells, epiblast).

Suitable primary embryonic cells (i.e primitive neuroectodermal cells) should be dissected from the early neural plate, preferably as soon as this structure can be identified. In mice, this is typically at stage E7.5-E7.75; in humans, this is the 0-5 somite stage or Carnegie stage 7-9. In some embodiments the primary embryonic cells are dissected from the mouse embryo before stage E10, such as before stage E9, for example before stage E8.5, E8.0, E7.75 or before stage E7.5. In some embodiments the primary embryonic cells are dissected from the human embryo before Carnegie stage 10, such as before stage 9, for example before stage 8.5, 8.0, 7.5 or before Carnegie stage 7.0.

Pluripotent cells such as mouse or human ES or iPS cells, or mouse epiblast stem cells may also be used as a starting point. Epiblast stem cells are believed to represent E5.5 in the mouse. They can be derived from embryos or from mouse ES cells which represent E3.5.

When using epiblast stem cells, the cells are typically maintained in pluripotent state by culturing with fibronectin and in the presence of FGF2 and Activin. To derive NPSCs, FGF4 is added to the culture medium and the cells cultured until colonies with neural plate morphology emerge; this typically occurs after 4-6 passages (12-18 days). At this stage, FGF2 and Activin are removed from the culture medium. The obtained NPSCs can be maintained by culture with FGF4.

In an alternative method, NPSCs may be derived from epiblast stem cells by culturing the cells in culture media containing FGF4 as the only growth factor present in the culture media (i.e. in the absence of FGF2 and/or activin). In this method there is significant cell death. The obtained NPSCs can be maintained by culture with FGF4.

In yet other another method, NPSCs may be derived from epiblast stem cells by overgrowth of epiblast cells followed by removal of all growth factors at 50% confluence. Fresh media is added (not changed) every 2-3 days. After ~7 days neural cell clusters can be observed and cultured in FGF4 to obtain NPSCs.

In a yet further method, NPSCs may be derived from epiblast cells by growing cells in suspension culture in the presence of FGF4 (and the absence of FGF2 and activin) until aggregates form. The aggregate culture is then supplemented with fibronectin daily for 3-4 days, after which the aggregates begin to adhere and spread. NPSCs can then be observed.

When using (e.g human) ES or iPS cells, FGF2 and activin may also be used as described above for epiblast stem cells. However, when using ES or iPS cells, NPSCs may be derived by culturing the cells in culture media containing FGF4 as the only growth factor present in the culture media (i.e. in the the absence of exogenously added FGF2 and/or activin) without significant cell death. The obtained NPSCs can be maintained by culture with FGF4.

Characteristics of NPSCs

Unlike neural precursors from older embryos and the adult, which have consistently been shown to be supported by FGF2 and EGF, the proliferation and stem cell (i.e. undifferentiated) state of NPSCs is maintained by FGF4. As noted previously, a specific effect for FGF4 has not been shown previously for any neural precursor or stem cell. Importantly, neither FGF2 nor EGF have any effect on the proliferation of neural plate stem cells.

In addition to the absence of a proliferative effect of EGF or FGF2, a number of other FGFs tested (FGFs 2, 5, 8, 9, 10, 19) do not increase the proliferation of NPSCs.

Importantly, not only does FGF4 cause NPSCs to proliferate, it also arrests their differentiation in an early 'pre-patterned' state. This state is characterized by expression of the marker Brn-2 in 100% of NPSCs, along with expression of the marker Sox-1 in ~30% of the cells in a NPSC population. In some embodiments, less than 95% of the NPSC population expresses Sox-1, for example less than 85%, 75%, 65%, 55%, 45%, 35%, 25%, 15% or less than 5%.

NPSCs are also characterized by the fact that they do not express the neurogenic bHLH factors Ngn2 and MASH1. Most NPSCs also do not express the neurogenic zinc finger facto PLZF; in some embodiments less than 10% of the NPSC population expresses PLZF, for example less than 9%, 8%, 7%, 6%, 5%, 4%, 3%, 2% or less than 1%. In some embodiments NPSCs do not express PLZF (i.e. 0% of the NPSC population expresses PLZF). Thus, in some embodiments the NPSC does not express one or more of the markers selected from the group of PLZF, ngn2 or MASH1.

NPSCs are also characterized by the fact that they do not express pax3, a marker of BMP-2 activity. NPSCs may also be characterized by the fact that they do not express the markers Pax6, En1, En2, and/or Krox20.

In the presence of FGF4, NPSCs are maintained in a 'pre-patterning' state, where they are not responsive to the dorsoventral patterning signals of Sonic hedgehog (Shh) and BMP-2. NPSCs cultured in the presence of FGF4+Shh do not express the marker of Shh activity, Nkx2.2. Similarly, NPSCs cultured in the presence of FGF4+BMP-2 do not express the marker of BMP-2 activity, Pax3.

Accordingly, the present invention provides an isolated neural plate stem cell, characterised in that:—
  (i) FGF4 increases the proliferation of the NPSC; and
  (ii) FGF2 does not increase the proliferation of the NPSC.

In some embodiments, the rate of proliferation of the NPSC in the presence of FGF4 is more than twice the rate of proliferation observed in the absence of exogenous growth factors (e.g. the rate of proliferation observed for NPSCs cultured only in N2 medium).

For example, the rate of proliferation of the NPSCs in the presence of FGF4 may be more than three-fold the rate of proliferation observed in the absence of exogenous growth factors, such as more than four-fold, more than five-fold, or more than 6-fold. Proliferation of the NPSC may be measured by, for example, measuring the proportion of cells which incorporate Bromodeoxyuridine (BrdU) in a defined time window (see, for example, FIG. 1).

The invention also provides provides an isolated neural plate stem cell, characterised in that culturing in FGF4 maintains the NPSC in a pre-patterning state and FGF2 does not maintain the NPSC in a pre-patterning state.

In this respect, a "pre-patterning state" is a state where the NPSC expresses the marker Brn-2 and does not express the neurogenic bHLH factors Ngn2 and MASH1. In the "pre patterning state, the NPSC is not responsive to the dorsoventral patterning signals of Sonic hedgehog (Shh) and BMP-2.

In some embodiments the NPSC is further characterized by expression of brn2.

In some embodiments the NPSC is yet further characterized by the absence of Ngn2 and/or MASH1 expression.

In some embodiments the NPSC is characterized by the absence of Pax3 expression.

In some embodiments the NPSC is yet further characterized by the absence of Pax6, En1, En2, and/or Krox20 expression.

In some embodiments, the NPSC is characterized by the absence of the neural rosette marker, PLZF (Elkabetz 2008, Genes Dev). Thus, in some embodiments the neural plate stem cell does not express one or more of the markers selected from the group of PLZF, ngn2 or MASH1.

In another embodiment, the present invention provides an isolated population of neural plate stem cells, characterized in that substantially all of the cells in the population express brn2.

In some embodiments, less than 95% of the cells in the population express sox1. In some embodiments, less than 90% of the NPSC population expresses Sox-1, for example less than 85%, 75%, 65%, 55%, 45%, 35%, 25%, 15% or less than 5%.

In some embodiments the NPSC population is further characterized by the absence of PLZF, Ngn2 and/or MASH1 expression.

In some embodiments the NPSC population is characterized by the absence of Ngn2 and/or MASH1 expression; for example, in some embodiments less than 10% of the NPSC population expresses MASH1, for example less than 9%, 8%, 7%, 6%, 5%, 4%, 3%, 2% or less than 1% of the population. In some embodiments none (i.e. 0%) of the NPSC population expresses MASH1.

In some embodiments the NPSC population is characterized by the absence of Pax3 expression; for example, in some embodiments less than 10% of the NPSC population expresses MASH1, for example less than 9%, 8%, 7%, 6%, 5%, 4%, 3%, 2% or less than 1% of the population. In some embodiments none (i.e. 0%) of the NPSC population expresses MASH1.

In some embodiments the NPSC population is yet further characterized by the absence of Pax6, En1, En2, and/or Krox20.

In some embodiments the presence of FGF4 increases the proliferation of the cell population and FGF2 does not increase the proliferation of the cell population. The present invention provides an isolated neural plate stem cell population substantially as hereinbefore described with reference to any of the Examples herein.

Differentiation of NPSCs into Neural Cell Types

In the presence of FGF4, NPSCs are maintained in a 'pre-patterning' state, where they do not express neurogenic factors such as PLZF, Pax3, Pax6, En1, En2, Krox20, Ngn2 and MASH1. However, on removal of FGF4, NPSCs begin to differentiate into neural cell types, as can be seen by their formation into neural rosettes (which are characteristic of later neural cells from the neural tube) which subsequently differentiate into neurons.

Once FGF4 is removed, NPSCs are able to differentiate into dopamine and serotonin neurons, as well as motorneurons, even after numerous passages. In addition, once FGF4 is removed, expression of markers such as Pax3 is observed. On culture with Shh and FGF8, NPSCs are observed to differentiate into neurons expressing expressing tyrosine hydroxylase, characteristic of catecholaminergic neurons such as dopamine neurons, or serotonin neurons (see FIG. 10). Similarly, culture of NPSCs with retinoic acid results in neurons expressing homeobox-9 (HB-9), characteristic of motor neurons (see FIG. 11)

Accordingly, the present invention provides an isolated neural plate stem cell which is capable of differentiation into a dopamine or serotonin neuron (as characterized by the expression of tyrosine hydroxylase) when cultured in the presence of Shh and FGF8 and the absence of FGF4.

It is believed that, because of the very early developmental stage of NPSCs, they are capable of differentiation into any, or a very broad range of, neural or glial cell type. For example, NPSCs may be capable of differentiation into cholinergic neurons, motor neurons, adrenergic neurons, noradrenergic neurons, peptidergic neurons, glial cells, astrocytes and/or oligodendrocytes.

The present invention also provides an isolated neural plate stem cell which is capable of differentiation into motor neuron (as characterized by the expression of HB-9) when cultured in the presence of retinoic acid the absence of FGF4.

In some embodiments, members of a NPSC population are capable of differentiation into monoaminergic neuron or motor neuron after at least 40 passages.

Definitions

The term "neural plate morphology" is used herein to describe features of NPSCs including: epithelial morphology (formation of the cells into sheets), large nuceli and/or a high nucleus to cytoplasm ratio. In some embodiments the diameter of the nucleus at its widest point is over 20% of the diameter of the cell at its widest point, for example over 30% of the diameter of the cell at its widest point, such as over 40%, 50%, 60%, 70%, 80% or over 90% of the diameter of the cell at its widest point.

The terms "in the presence of" and "in the absence of" are used herein with reference to culturing cells with or without specific growth factors (such as FGF2 and FGF4) or with or without certain components of the culture medium (such as without fibronectin). For the avoidance of doubt, culturing cells "in the presence of" a named factor is intended to mean that the named growth factor has been exogenously added to the culture medium; cells cultured in media in which a trace amount of the factor has been secreted by the cultured cells it is not considered to be cultured "in the presence of" that factor.

Similarly, "in the absence of" a named factor or component is intended to mean that the named growth factor has not been exogenously added to the culture medium; thus, cells cultured in media into which trace amounts of a growth factor have been secreted by the cultured cells are still consider to be cultured "in the absence of" the factor. Thus, when a cell is cultured "only" with FGF4, it means that FGF4 is the only growth factor which has been exogenously added to the media other than growth factors which are normally included in the media (for example, the N2 media in which the NPSCs are typically grown includes insulin, a factor which is very important for the survuival of neural cells).

In some embodiments, growth factors or components which are present in the media are present at a concentration of over 5 ng/ml, for example over 10, 15, 20, 25, 30, 35, 40, 45 or over 50 ng/ml. Growth factors or component under this concentration are considered "absent".

In practice, "removal" of FGF2 and/or activin from media as used herein is achieved by replacing the medium containing FGF2 and/or activin with medium containing, for example, only FGF4.

"Substantially all" cells in a population as defined herein is used to mean over 95% of the cells in a population, such as more than 96%, more than 97%, more than 98% or more than 99% of the cells.

EXAMPLES

The invention is described in specific embodiments with reference to the accompanying drawings, in which:

FIG. 1 shows the effects of FGFs on Proliferation and Survival of E7.5 CNS Progenitors Legend: Cells were dissociated in 0.5% trypsin and plated into N2+FGF4+Trypsin Inhibitor (2 mg/ml, from Chicken Egg white [Sigma, T-2011]).

N2 media change+FGF4 at 24 hours. At 48 hours, N2 media change+specified FGF. After 1 hour, BrdU added. Cells sit for an additional hour, then fixed.

FIG. 2 shows the In vitro Culture of E8.5 Neural Stem Cells

Legend: E8.5 dissociated ventral midbrain cultured in the presence of Shh (500 ng/ml) and FGF8 (100 ng/ml). Cells were photographed 5 days after plating.

FIG. 3 shows the production of NPSCs from pluripotent cells

Legend:

Step 1. Pluripotent cell conditions (FGF2+Activin for epiblast cells)+FGF4.

Step 2. Cells look like epiblast cells with minor differences in morphology.

Step 3. After 4-6 passages (12-18 days), Colonies with neural plate morphology emerge. FGF2 and Activin are removed.

Cells are serially passaged with Accutase in N2+FGF4 or N2+FGF4+BMP4 (up to 41 passages, so far). Alternatively, passaging cells with Collagenase preserves the neural plate morphology of the primary cells.

FIG. 4 shows methods for producing NPSCs from epiblast stem cells

Legend: Overgrowth of mouse epiblast cells. All growth factors are removed at 50% confluence. Medium added every 2-3 days, but is not completely changed.

There is not very much cell death. After 7 days many clusters of neural plate cells can be observed and expanded with FGF4. In the absence of FGF4, a subpopulation of different cells are observed (the identity of these non-neural cells is not known at this time).

Alternatively, Epiblast cells can be grown under non-adherent conditions in N2+FGF4. Within 48-72 hours, aggregates are observed. The aggregate cultures are supplemented with fibronectin daily. After 3-4 days the aggregates adhere and begin to spread. Neural plate stem cells are observed.

FIG. 5 shows that FGF4 suppresses the Expression of Neurogenic Transcription Factors Legend: MASH1 polyclonal antibody (1:1,000) generously provided by J. Johnson.

Ngn2 monoclonal antibody (1:50) generously provided by D. J. Anderson.

Sox1 polyclonal antibody (1:200) generously provided by R. Lovell-Badge.

PLZF polyclonal antibody (1:50) obtained from Calbiochem.

FIG. 6 shows the derivation of Neural Progenitors from Human ES cells

Legend: (Top three panels) The appearance of neural plate cells derived from human embryonic stem cells. Note the neuroepithelial nature of the colonies and the density of the cells. (Graph) Just like primary mouse neural plate cells, neural plate cells derived from human embryonic stem cells proliferate specifically in response to FGF4 (compare to FIG. 1).

FIG. 7 shows that FGF4 suppresses the Morphogenic Response of Shh and BMP2

Legend: Nkx2.2 (T. Jessell) and Pax3 (C. Ordahl) monoclonal antibodies from DSHB. Used at 1:20. BMP+FGF4 still has a pro-survival effect. The neural plate cells don't exhibit patterning characteristic of cells derived from the later embryo. FGF4 suppresses the effect of sonic hedgehog (Shh) and BMP2. However in the absence of FGF4 the cells further differentiate and the expected morphogenic response to Shh and BMP2 is seen.

FIG. 8 shows the differentiation of NPSCs to Neurons in the absence of FGF4

Legend: 18 days growth factor (FGF4) withdrawal (p+19). Tuj1=monoclonal antibody binding neuronal beta-tubulin; TH=tyrosine hydroxylase. 7 days growth factor (FGF4) withdrawal (p+23) at low density Many undifferentiated cells can still be observed FIG. 9 shows the induction of Dorsoventral Identities by Morphogens in the Absence of FGF4

Legend: Msx1 (T. Jessell) monoclonal antibody from DSHB. Used at 1:20. Nkx6.1 polyclonal antibody (1:400) generously provided by M. German. This data shows the Neural plate stem cells do not, for example, express the dorsal marker Pax3 when cultured in the presence of FGF4. However, Pax3 expression is observed when FGF4 is withdrawn.

FIG. 10 shows that treatment with Shh leads to an Increase in Monoaminergic Neurons Legend: TH polyclonal antibody (Pel-freez, 1:400). Pitx3 polyclonal antibody (Zymed, 1:400) 5-HT rabbit polyclonal antibody (Sigma, 1:4,000). Lmx1b gp polyclonal antibody (1:4,000) generously provided by T. Jessell.

FIG. 11 shows that Retinoic Acid-Treated Progenitors Differentiate to Putative Motor Neurons Legend: Tuj1 polyclonal antibody (Covance, 1:400). Hb9 (T. Jessell) monoclonal antibody from DSHB. Used at 1:20.

FIG. 12 shows floor plate induction of neural plate cells. Increasing doses of Shh are able to induce Foxa2, a marker of the floor plate, in neural plate stem cells. Inhibition of MAPK signaling is able to enhance the percentage of Foxa2 induction by Shh. Floor plate cells give rise to dopamine neurons.

FIG. 13 shows derivation of Neural Plate Stem Cells on a variety of extracellular matrices in monolayer culture Legend: Human induced pluripotent cell (hIPS) line, KIPS, were grown by standard protocols in human embryonic stem cell medium plus FGF2 and activin on mouse embryonic feeders (MEFs). At passage 26, hIPS colonies were passaged using collagenase. Colonies were separated from MEFs by gravity in a 15 mL conical tube containing hES medium. Cells were subsequently replated into 12 well-plates containing N2 medium plus FGF4 (100 ng/mL) and the well plates were coated either with fibronectin, laminin, or gelatin. The fibronectin and laminin-coated plates were pre-coated with polyornithine. After four days, the cells were fixed in cold 4% paraformaldehyde and stained by immunofluorescence for the neural plate marker, Brn2, and the apoptosis marker, cleaved caspase-3.

The results show that Neural Plate Stem Cells (NPSCs) are successfully derived on laminin and gelatin-coated plates.

FIG. 14 shows clonal growth of neural plate stem cells

Legend: Single neural plate neural stem cells were plated at low density and grown into clonally derived neural plate stem cell colonies (one colony is shown). Individual colonies were selected and expanded to form clonal neural plate stem cell lines. So far, the clonal neural plate stem cell lines which have been tested are all able to give rise to neurons, including dopamine and serotonin neurons.

FIGS. 15 & 15A show expression of Sox1 and Brn2 in the Neural Plate

Legend: Sox1 has been believed to be the earliest marker of the neural lineage. However, the inventors have found that Sox1 is not a good marker for neural plate stem cells and that, in fact, Sox1 is actually not a good marker for the early neural plate in vivo. The figures shown illustrate the expression of Sox1 and Brn2 in the early embryo by immunohistochemistry. (FIG. 15) Sox1 is not expressed in the early neural plate. Sox1 is observed to be restricted to the ventral midline at intermediate neural plate stages. (FIG. 15A(A)) Sox1 is first seen to be expressed in precisely two rows of cells at the midline. (FIG. 15A(B)) Unlike Sox1, Brn2 is widely expressed throughout the neural plate at comparable stages.

FIG. 16 shows NPSC transplantation to a Chick Embryo

Legend: Images of neural plate cells injected into the neural plate of a chicken embryo. The chicken embryos were left for several days and sacrificed at midgestation. In both images, it is clear that the neural plate cells have differentiated into neurons. (A) GFP-labeled mouse neural plate cell-derived neuron. (B) Human neural plate-derived neuron stained with a human nuclear antigen. The neuron is also tyrosine hydroxylase-positive (TH) which is an enzyme involved in dopamine synthesis, a catecholamine centrally involved in Parkinson's disease.

FIG. 17 shows NPSC transplantation into Neonatal Rat Hindbrain

Legend: Neural plate cells injected into neonatal rat cortex. (A) survival of mouse antigen specific cells, stained with a mouse-specific antibody at the edge of the graft (mouse-negative cells at the bottom of the image are easily accounted). (B) & (C) Grafts of human cells into rat brains. (B) Numerous Tuj1+ young+ neurons and GFAP+ glia within the graft. (C) Several TH+ putative, dopamine neurons can be seen, as well as one serotonergic (5-HT) cell.

MATERIALS AND METHODS

The composition of the N2 medium described herein is as set out in Bottenstein and Sato. 1979.

Example 1

Derivation of Neural Plate Stem Cells from the Mouse Embryo

Mouse headfold-stage embryos (E7.5-E7.75) were removed from the uteri of timed, pregnant mothers. The anterior neural plate was dissected away from the visceral endoderm, head mesenchyme, and the developing foregut and heart primordium. Cells were dissociated and placed in N2 medium on fibronectin-coated dishes.

Unlike rosette-forming cells taken from later-staged embryos or derived from pluripotent cells (Elkabetz et al. 2008; Koch et al. 2009), the neural plate stem cells form colonies of flat, continuous epithelium. The neural plate stem cells, like embryonic stem cells, have large, prominent nuclei and a high nucleus-to-cytoplasm ratio. Sox1-expressing cells are present and the non-neural markers, Oct4, brachyury, and Sox17, are all absent.

At various, later stages, FGF2 and EGF have been shown to support the multipotent state and proliferation of neural stem cells (Cattaneo and McKay 1990; Pollard 2008). In contrast, neither FGF2 nor EGF maintained the neural plate stem cells in their undifferentiated state. Either in the presence or absence of FGF2, neural plate stem cells derived from mouse embryos begin to form rosette structures (Elkabetz et al. 2008, Koch et al. 2009) within 48 hours; these rosettes differentiate to form neurons within one week.

We screened a number of fibroblast growth factors and found, to our surprise, that FGF4 has a potent and specific mitogenic effect on neural plate stem cells that is not mimicked by other FGFs. In addition, as measured by immunohistochemistry for cleaved caspase-3, FGF4 promotes the survival of neural plate stem cells.

Example 2

Derivation of Neural Plate Stem Cells from Mouse and Human Pluripotent Cells

We sought to derive neural plate stem cells from mouse pluripotent cells. Mouse epiblast cells were maintained in N2 medium on fibronectin in the presence of FGF2 and activin. Under these conditions, cultures were supplemented with FGF4.

In separate experiments, neural plate stem cells have been derived directly from human pluripotent cells (hEs and iPS) through culture in N2 medium supplemented with only FGF4 (i.e. in the absence of FGF2, activin or any other growth factor).

Aside from the mitogenic properties of FGF4 on neural plate stem cells, FGF4 has also been implicated in the differentiation of pluripotent cells (Kunath 2007, Stavridis et al. 2007) and FGFs are believed to have a role in neural induction (Stern; Pera et al. 2003).

Initially, the epiblast stem cells appear polarized upon FGF4 treatment. It is not clear if the development of a bipolar morphology is indicative of a transition in cell state to ectoderm, or if this is merely a change in cell shape.

After 4-6 passages (roughly 12-18 days), colonies with a neural plate morphology appear, at which time FGF2 and activin are removed. Continued application of FGF2 and activin, at this stage, leads to the development of homogeneous non-neural cells; the identity of these non-neural cells is not known at this time.

The resulting pluripotent cell-derived neural plate stem cells are grown on fibronectin in N2 medium plus FGF4 and passaged using accutase.

Neural plate stem cells can be derived from mouse epiblast stem cells in N2 plus FGF4, in the absence of FGF2 and activin. In this case, colonies with neural plate morphology can be observed more rapidly (approximately one week) but this is accompanied by massive cell death in the cultures.

Like neural plate stem cells derived from the embryo, the pluripotent-cell derived NPSC's do not express markers of non-neural lineages and, when FGF4 is removed, they form rosettes en route to neuronal differentiation. Differentiation to neurons has been observed from neural plate stem cells passaged up to 41 times.

The key feature of the methods of deriving NPSC's is the step of culturing the precursor cells (epiblast stem cells, ES, iPS, primary embryonic) with FGF4. Some example methods comprising this step for deriving NPSC's from epiblast stem cells are outlined in FIG. 4.

Sox1 is believed to be the earliest marker of the definitive neural lineage in the vertebrate (Pevny 1998). While Sox1 expression is observed by immunohistochemistry in neural plate stem cells, it is only seen in about 30% of the cells and there is some variation in the intensity of nuclear staining. We find that when FGF4 is removed, Sox1 is expressed in nearly all of the resulting rosette cells at 48 hours.

In addition, the neurogenic bHLH transcription factors, MASH1 and Ngn2 (Parras 2002) which are not expressed in the neural plate, are also induced after 48 hours of FGF4 withdrawal. Finally, in a similar vein, the neural rosette marker, PLZF, is upregulated after FGF4 withdrawal. These results indicate that Sox1 may not be a distinctive marker for the early neural plate.

We investigated Sox1 expression in the mouse neural plate by immunohistochemistry. To our surprise, Sox1 is not expressed in the neural plate when it is initially formed; instead, Sox1 is first seen at intermediate neural plate stages when it is restricted to the two rows of hinge-forming cells at the ventral midline of the neural plate which initiate neural tube closure (Smith J L 1991). Even at later stages, sox1 is expressed weakly, if at all, in the lateral neural plate (Thomas Andreska, R. K., and A. G. S, in preparation). In contrast, the POU-domain and homeodomain-containing transcription factor, Brn2/Pou3f2 is expressed throughout the neural plate from the earliest stages and is uniformly expressed in vitro in neural plate stem cells.

Example 3

Patterning of Neural Plate Stem Cells.

In order to specifically drive the differentiation of neural progenitors, they should be responsive to secreted factors which pattern the neural tube. For the dorsoventral axis of the neural tube, the floor plate and roof plate organizers secrete sonic hedgehog (shh) and bone morphogenetic proteins which have ventralizing and dorsalizing activities, respectively.

Markers of dorsoventral identity are not expressed in the open neural plate (Shimamura 1997; Liem 1995) but are induced at approximately E8.25 in the closed or almost closed neural tube. Similarly, neural plate stem cells do not express markers of dorsoventral identity in the presence of FGF4 and merely adding Shh or BMP2 is not sufficient to induce Nkx2.2, a ventral marker, or Pax3, a dorsal marker, respectively. If FGF4 is withdrawn, just as Sox1 and bHLH factors are induced, dorsoventral markers are similarly upregulated and, under these conditions, Shh induces Nkx2.2 and BMP2 induces Pax3. FGF4 seems to maintain neural plate stem cells in an unpatterned state, a state before they acquire the competence to be patterned by Shh or BMP-2.

Morphogens like Shh act in a concentration-dependent manner. In a larger experiment, we grew neural plate stem cells, withdrawn from FGF4, in three different concentrations of Shh (0 ng/ml, 500 ng/ml, and 1 ug/ml) and also in BMP-2 and assessed the expression of four dorsoventral markers.

As the concentration of Shh is increased, ventral markers (Nkx2.2 and Nkx6.1) are induced at the expense of the dorsal marker (Pax3); upon BMP2 treatment, the opposite effect is observed. In addition, under these conditions, the roof plate marker, Msx1, is only induced upon BMP2 treatment. Similar observations have been made in the spinal cord and midbrain of the intact embryo (Briscoe 2000; Agarwala 2001), in primary neural tube explants (Wijgerde 2002) and dissociated progenitors (Kittappa 2007), and in differentiating mouse embryonic stem cells (Wichterle 2002). Neural plate stem cells, released from the effects of FGF4, are fully capable of responding to patterning by ventralizing and dorsalizing morphogens.

REFERENCES

Abell A N, Granger D A, Johnson N L, Vincent-Jordan N, Dibble C F, Johnson G L. *Trophoblast stem cell maintenance by fibroblast growth factor 4 requires MEKK4 activation of Jun N-terminal kinase*. Mol Cell Biol. 2009 May; 29(10):2748-61.

Agarwala S, Sanders T A, Ragsdale C W. *Sonic hedgehog control of size and shape in midbrain pattern formation*. Science. 2001 Mar. 16; 291(5511):2147-50.

Bottenstein J E, Sato G H. *Growth of a rat neuroblastoma cell line in serum-free supplemented medium*. Proc Natl Acad Sci USA. 1979 January; 76(1):514-7.

Briscoe J, Pierani A, Jessell T M, Ericson J. *A homeodomain protein code specifies progenitor cell identity and neuronal fate in the ventral neural tube*. Cell. 2000 May 12; 101(4):435-45.

Castranio T, Mishina Y. *Bmp2 is required for cephalic neural tube closure in the mouse*. Dev Dyn. 2009 January; 238(1):110-22.

Cattaneo E, McKay R. *Proliferation and differentiation of neuronal stem cells regulated by nerve growth factor*. Nature. 1990 Oct. 25; 347(6295):762-5.

Chen C W, Liu C S, Chiu I M, Shen S C, Pan H C, Lee K H, Lin S Z, Su H L. *The signals of FGFs on the neurogenesis of embryonic stem cells*. J Biomed Sci. 2010 Apr. 29; 17:33.

Conti L, Pollard S M, Gorba T, Reitano E, Toselli M, Biella G, Sun Y, Sanzone S, Ying Q L, Cattaneo E, Smith A. *Niche-independent symmetrical self-renewal of a mammalian tissue stem cell*. PLoS Biol. 2005 September; 3(9):e283.

Elkabetz Y, Panagiotakos G, Al Shamy G, Socci N D, Tabar V, Studer L. *Human ES cell-derived neural rosettes reveal a functionally distinct early neural stem cell stage*. Genes Dev. 2008 Jan. 15; 22(2):152-65

Forsberg M, Holmborn K, Kundu S, Dagalv A, Kellen L, Forsberg-Nilsson K. *Under-sulfation of heparan sulfate restricts the differentiation potential of mouse embryonic stem cells*. J Biol Chem. 2012 Feb. 1.

Gritti A, Parati E A, Cova L, Frolichsthal P, Galli R, Wanke E, Faravelli L, Morassutti D J, Roisen F, Nickel D D, Vescovi A L. *Multipotential stem cells from the adult mouse brain proliferate and self-renew in response to basic fibroblast growth factor*. J Neurosci. 1996 Feb. 1; 16(3):1091-100.

Johe K K, Hazel T G, Muller T, Dugich-Djordjevic M M, McKay R D. *Single factors direct the differentiation of stem cells from the fetal and adult central nervous system*. Genes Dev. 1996 Dec. 15; 10(24):3129-40.

Kittappa R, Chang W W, Awatramani R B, McKay R D. *The foxa2 gene controls the birth and spontaneous degeneration of dopamine neurons in old age*. PLoS Biol. 2007 December; 5(12):e325.

Koch P, Opitz T, Steinbeck J A, Ladewig J, Brüstle O. *A rosette-type, self-renewing human ES cell-derived neural stem cell with potential for in vitro instruction and synaptic integration*. Proc Natl Acad Sci USA. 2009 Mar. 3; 106(9):3225-30.

Kosaka N, Kodama M, Sasaki H, Yamamoto Y, Takeshita F, Takahama Y, Sakamoto H, Kato T, Terada M, Ochiya T. *FGF-4 regulates neural progenitor cell proliferation and neuronal differentiation*. FASEB J. 2006 July; 20(9):1484-5.

Kunath T, Saba-El-Leil M K, Almousailleakh M, Wray J, Meloche S, Smith A. *FGF stimulation of the Erk1/2 signalling cascade triggers transition of pluripotent embryonic stem cells from self-renewal to lineage commitment*. Development. 2007 August; 134(16):2895-902.

Liem K F Jr, Tremml G, Roelink H, Jessell T M. *Dorsal differentiation of neural plate cells induced by BMP-mediated signals from epidermal ectoderm*. Cell. 1995 Sep. 22; 82(6):969-79.

Mayshar Y, Rom E, Chumakov I, Kronman A, Yayon A, Benvenisty N. *Fibroblast growth factor 4 and its novel splice isoform have opposing effects on the maintenance of human embryonic stem cell self-renewal*. Stem Cells. 2008 March; 26(3):767-74.

Parras C M, Schuurmans C, Scardigli R, Kim J, Anderson D J, Guillemot F. *Divergent functions of the proneural genes Mash1 and Ngn2 in the specification of neuronal subtype identity*. Genes Dev. 2002 Feb. 1; 16(3):324-38.

Pera E M, Ikeda A, Eivers E, De Robertis E M. *Integration of IGF, FGF, and anti-BMP signals via Smad1 phosphorylation in neural induction*. Genes Dev. 2003 Dec. 15; 17(24):3023-8.

Pevny L H, Sockanathan S, Placzek M, Lovell-Badge R. *A role for SOX1 in neural determination*. Development. 1998 May; 125(10):1967-78.

Pollard S M, Wallbank R, Tomlinson S, Grotewold L, Smith A. *Fibroblast growth factor induces a neural stem cell phenotype in foetal forebrain progenitors and during embryonic stem cell differentiation*. Mol Cell Neurosci. 2008 July; 38(3):393-403.

Rathjen J, Haines B P, Hudson K M, Nesci A, Dunn S, Rathjen P D. *Directed differentiation of pluripotent cells to neural lineages: homogeneous formation and differentiation of a neurectoderm population*. Development, 2002; 129:2649-61

Reynolds B A, Weiss S. *Generation of neurons and astrocytes from isolated cells of the adult mammalian central nervous system.* Science. 1992 Mar. 27; 255(5052):1707-10.

Reynolds B A, Tetzlaff W, Weiss S. *A multipotent EGF-responsive striatal embryonic progenitor cell produces neurons and astrocytes.* J Neurosci. 1992 November; 12(11):4565-74.

Shimamura K, Rubenstein J L. *Inductive interactions direct early regionalization of the mouse forebrain.* Development. 1997 July; 124(14):2709-18.

Smith J L, Schoenwolf G C. *Further evidence of extrinsic forces in bending of the neural plate.* J Comp Neurol. 1991 May 8; 307(2):225-36.

Stavridis M P, Lunn J S, Collins B J, Storey K G. *A discrete period of FGF-induced Erk1/2 signalling is required for vertebrate neural specification.* Development. 2007 August; 134(16):2889-94.

Streit A, Berliner A J, Papanayotou C, Sirulnik A, Stern C D. *Initiation of neural induction by FGF signalling before gastrulation.* Nature. 2000 Jul. 6; 406(6791):74-8.

Tanaka S, Kunath T, Hadjantonakis A K, Nagy A, Rossant J. *Promotion of trophoblast stem cell proliferation by FGF4.* Science. 1998 Dec. 11; 282(5396):2072-5.

Vescovi A L, Reynolds B A, Fraser D D, Weiss S. *bFGF regulates the proliferative fate of unipotent (neuronal) and bipotent (neuronal/astroglial) EGF-generated CNS progenitor cells.* Neuron. 1993 November; 11(5):951-66.

Weiss S, Dunne C, Hewson J, Wohl C, Wheatley M, Peterson A C, Reynolds B A. *Multipotent CNS stem cells are present in the adult mammalian spinal cord and ventricular neuroaxis.* Neurosci. 1996 Dec. 1; 16(23):7599-609.

Wichterle H, Lieberam I, Porter J A, Jessell T M. *Directed differentiation of embryonic stem cells into motor neurons.* Cell. 2002 Aug. 9; 110(3):385-97.

Wijgerde M, McMahon J A, Rule M, McMahon A P. *A direct requirement for Hedgehog signaling for normal specification of all ventral progenitor domains in the presumptive mammalian spinal cord.* Genes Dev. 2002 Nov. 15; 16(22):2849-64.

The invention claimed is:

1. An in vitro method of obtaining and maintaining isolated neural plate stem cells (NPSC), comprising:
   (a) providing pluripotent cells or primitive neurectodermal cells in dissociated form;
   (b) culturing the cells in the presence of FGF4 for a sufficient amount of time to obtain an isolated NPSC by detecting the expression of the marker Brn-2 and not detecting the expression of the markers Ngn2, MASH1, Pax3, Pax6, En1, En2, and Krox20 on the NPSC, and
   (c) maintaining the isolated NPSC in culture in the presence of FGF4, wherein the NPSCs maintain the expression of Brn-2 and do not express Ngn2, MASH1; Pax3; Pax6; En1; En2; and Krox20.

2. The method of claim 1 wherein the pluripotent cells or primitive neurectodermal cell is a primary embryonic cell obtained from the early neural plate.

3. The method of claim 1 wherein the pluripotent cell is an epiblast stem cell, an embryonic stem cell, or an induced pluripotent cell.

4. The method of claim 3 wherein the pluripotent cell is cultured in the presence of FGF2 and/or Activin in addition to FGF4.

5. The method of claim 1 wherein the pluripotent cell or primitive neurectodermal cell is cultured in the presence of FGF4 and in the absence of FGF2 and/or Activin.

6. The method of claim 5 wherein the pluripotent cell or primitive neurectodermal cell is cultured in serum free medium containing exogenous FGF4.

7. The method of claim 1, wherein the isolated NPSC is maintained in culture for at least 40 passages.

8. The method of claim 1, wherein the NPSC are cultured in the presence of an extracellular matrix.

9. The method of claim 8, wherein the extracellular matrix comprises one or more component selected from the group consisting of fibronectin, laminin and gelatin.

10. An in vitro method of differentiating NPSCs into dopaminergic or serotonergic neurons, the method comprising:
    (a) obtaining NPSCs by the method of claim 1,
    (b) culturing the NPSCs in the presence of Shh and FGF8 in the absence of FGF4,
    (c) detecting tyrosine hydroxylase on the cultured cells, wherein serotonergic neurons that express tyrosine hydroxylase are produced.

11. An in vitro method of differentiating NPSCs into motor neurons, the method comprising
    (a) obtaining NPSCs by the method of claim 1, and
    (b) culturing the NPSCs in the presence of retinoic acid and in the absence of FGF4, and
    (c) detecting HB-9 on the cultured cells, wherein motor neurons expressing HB-9 are produced.

12. An in vitro method of maintaining a population of isolated neural plate stem cells (NPSCs) expressing Brn-2 in an undifferentiated state, comprising:
    (a) detecting Brn-2 but not Ngn2, MASH1; Pax3; En1; En2; and Krox20 on the population of isolated neural plate stem cells, and
    (b) culturing the NPSCs in neuronal medium comprising FGF4, wherein the NPSCs maintain expression of Brn-2 and do not express Ngn2, MASH1; Pax3; En1; En2; and Krox20.

13. The method of claim 12, wherein the neuronal medium is serum free medium.

14. The method of claim 12, wherein the neuronal medium is N2 medium.

15. The method of claim 12, wherein the NPSCs are derived from induced pluripotent stem cells (iPSCs) or embryonic stem cells (ESCs) by the steps of:
    culturing the iPSCs or ESCs cells in neuronal medium comprising FGF4 for a sufficient amount of time to differentiate the iPSCs or ESCs to NPSCs, and detecting expression of Brn-2 but not Ngn2, MASH1; Pax3; Pax6; En1; En2; and Krox20 on the NPSCs.

16. The method of claim 12, wherein the culturing step is in neuronal medium in the absence of FGF2 and activin.

17. The method of claim 12, wherein the NPSCs are derived from epiblast stem cells, wherein the NPSCs are derived by a method comprising:
    (a) culturing the epiblast stem cells in the presence of fibronectin, FGF2, Activin and FGF4 for a sufficient amount of time to form colonies with neural plate morphology,
    (b) subsequently culturing the cells of (a) in medium comprising FGF4 in the absence of additional factors to obtain NPSCs, and
    (c) detecting expression of Brn-2 and not Ngn2, MASH1; Pax3; Pax6; En1; En2; and Krox20 on the NPSCs.

18. The method of claim 12, wherein the FGF4 is present in an amount of at least 50 ng/ml.

* * * * *

UNITED STATES PATENT AND TRADEMARK OFFICE
CERTIFICATE OF CORRECTION

PATENT NO. : 10,160,951 B2
APPLICATION NO. : 14/395257
DATED : December 25, 2018
INVENTOR(S) : Raja Kittappa et al.

It is certified that error appears in the above-identified patent and that said Letters Patent is hereby corrected as shown below:

In the Specification

Column 16, Line 5, "Kellen" should be --Kjellen--.

Signed and Sealed this
Nineteenth Day of February, 2019

Andrei Iancu
*Director of the United States Patent and Trademark Office*